United States Patent
Maji

(10) Patent No.: US 11,883,227 B2
(45) Date of Patent: Jan. 30, 2024

(54) SYSTEMS AND METHODS FOR POWERING AN IMAGING SYSTEM

(71) Applicant: GE Precision Healthcare LLC, Wauwatosa, WI (US)

(72) Inventor: Goutam Maji, Bangalore (IN)

(73) Assignee: GE Precision Healthcare LLC, Wauwatosa, WI (US)

(*) Notice: Subject to any disclaimer, the term of this patent is extended or adjusted under 35 U.S.C. 154(b) by 237 days.

(21) Appl. No.: 17/193,541

(22) Filed: Mar. 5, 2021

(65) Prior Publication Data
US 2022/0280130 A1 Sep. 8, 2022

(51) Int. Cl.
A61B 6/00 (2006.01)
A61B 6/03 (2006.01)

(52) U.S. Cl.
CPC ........ *A61B 6/56* (2013.01); *A61B 6/032* (2013.01); *A61B 6/4435* (2013.01)

(58) Field of Classification Search
CPC ......... A61B 6/4435; A61B 6/56; A61B 6/032; A61B 6/03; A61B 6/035; A61B 6/40; A61B 8/56; A61B 6/405; A61B 6/4241; A61B 6/482; A61B 5/055; A61B 6/54; A61B 6/4014; H02J 3/32; H02J 9/062; H02J 7/0013; H02J 9/061; H02J 7/005; H02J 2310/23; H02J 7/02; H02J 9/068; H02J 7/345; H02J 7/04; H02J 7/00036; H02J 7/007; H02J 2207/50; H02J 2207/30; H02J 2207/20; H02J 7/00047; H02J 7/0021; H02J 7/0047; H02J 7/042; H02J 7/00714; H02J 7/0068; G01V 5/005; H05G 1/10; H05G 1/20; H05G 1/46; H05G 1/60; H05G 1/58; H01F 38/18; H02M 7/539; H02M 7/797; H02M 3/3353; H02M 1/44; H02M 3/04; H03K 17/6871; H01L 29/1608; H01L 27/0623; H02N 11/002; H02P 3/14; Y10T 29/49002; H01J 35/045; H01J 35/06; H01J 2235/068; G01R 33/28
USPC ...................................... 378/4, 19, 101–118
See application file for complete search history.

(56) References Cited

U.S. PATENT DOCUMENTS

| | | | |
|---|---|---|---|
| 5,808,376 A * | 9/1998 | Gordon ..................... | H02J 1/02 307/64 |
| 8,218,726 B2 * | 7/2012 | Bressel .................. | A61B 5/055 378/103 |
| 2015/0085969 A1 * | 3/2015 | Mekonnen ............... | A61B 6/56 378/4 |
| 2017/0085122 A1 * | 3/2017 | Nasiri ...................... | A61B 6/56 |
| 2018/0263591 A1 | 9/2018 | Shanthakumar | |

* cited by examiner

*Primary Examiner* — Irakli Kiknadze

(57) ABSTRACT

A power system and method for powering an imaging system. The power system and method include a power distribution unit (PDU) coupled to an imaging system gantry. An input of the PDU is electrically coupled to an alternating current (AC) power source from a utility power supply. An output of the PDU is electrically coupled to the imaging system gantry. The power system and method further include an energy storage system providing peak power to an X-ray generator of the imaging system during X-ray generation.

15 Claims, 6 Drawing Sheets

SYSTEMS AND METHODS FOR POWERING AN IMAGING SYSTEM

BACKGROUND

Embodiments of the subject matter disclosed herein relate to medical imaging systems, and more particularly, to addressing the power requirements of a computed tomography (CT) imaging system.

Various medical imaging systems and methods are used to obtain images of subjects for diagnosing the medical conditions of subjects. X-ray imaging systems may take many forms, such as a computed tomography (CT) imaging system and many other types of X-ray imaging systems that use X-rays for acquiring image data of subjects and generate user viewable images of the subjects.

Imaging a subject using a CT imaging system involves positioning a subject on a table, moving the table inside the gantry of the CT imaging system, and generating X-rays to pass through the subject in all directions to obtain images of the internal anatomy of the subject. The CT imaging system includes an X-ray generator that powers an X-ray tube for emitting X-rays through the subject positioned in the gantry of the CT imaging system and an X-ray detector array positioned to receive the X-rays. The X-rays received by the X-ray detector array are processed using various image reconstruction and visualization techniques to generate user viewable images of the subject. Although the total time taken for a CT scan usually varies between thirty to forty-five minutes, the time of actual X-ray exposure varies between a few seconds to a few minutes.

The highest power consumption of an X-ray generator is often referred as the "peak power" or "peak load" that is generated and consumed during the few seconds or few minutes of X-ray generation or X-ray exposure. A three-phase AC power source from a utility power supply is required to power the CT imaging system, including the X-ray generator, X-ray tube, and to meet the peak power demand of the CT imaging system.

In one example, during conventional CT imaging system operation, a 560 Volts direct current (VDC) bus may experience peak power demand of 28 kilo Watts (kW) during the X-ray generation or X-ray exposure, that causes the 560 VDC bus to have a current of around 62 Amps (A). However, during times of no X-ray generation or no X-ray exposure, the power demand is around 200-300 Watts (W). Also, to accommodate the peak power demand, all upstream CT imaging system components may be required to have the appropriate power ratings.

Different systems and methods are available for supplying peak power or backup power to a CT imaging system, such as an uninterruptible power supply (UPS), that provides the required uninterruptible power for the CT imaging system. However, these UPSs only provide a "back-up" for the entire CT imaging system and require a relatively larger area or space. Further, the existing power system components are designed for peak power consumption by the X-ray generator and all of the power components have the appropriate high power capability and ratings to supply the peak power. Also, bigger power supply infrastructure components like high-voltage direct current (HVDC) cables, high power rated components including fuses, alternating current to direct current (AC-DC) converters, soft-start circuits are required for supplying peak power.

Further, a power factor of a circuit is a phase shift between the voltage and the current. Theoretically, the maximum power factor value of one is highly desirable to reduce the amount of current drawn by the load. If the power factor of the circuit is less, a power factor correction (PFC) circuit may be provided to minimize the power loss. In a CT imaging system, a power distribution unit (PDU) supplies power to many different components of the CT imaging system, such as the axial drive to rotate the gantry, the X-ray generator and X-ray tube, and others. Owing to commercial infeasibility, it is not possible to provide the PFC circuit within the PDU. Therefore, the amount of power consumed by the CT imaging system is higher in absence of the PFC circuit.

Accordingly, there is a need for a power system and method that will provide the peak power to the CT imaging system and eliminate the peak load on the utility power supply with reduced space, consumption, and power ratings. Further, a system and method with an improved power factor and infrastructure footprint is highly desirable.

SUMMARY

In accordance with an aspect of the disclosure a power system for powering an imaging system. The power system comprising a power distribution unit (PDU) having at least one input and at least one output, the at least one input electrically coupled to an alternating current (AC) power source from a utility power supply; a gantry of the imaging system having at least one input, the at least one input electrically coupled to the at least one output of the PDU; and an energy storage system providing peak power to an X-ray generator of the imaging system during X-ray generation.

In accordance with an aspect of the disclosure an imaging system comprising a PDU with an input electrically coupled to a three-phase AC power source and at least one output; an imaging system gantry with at least one input electrically coupled to the at least one output of the PDU; and an energy storage system configured to store electrical energy and output the stored electrical energy to power an X-ray generator during an X-ray exposure.

In accordance with an aspect of the disclosure a method for powering an imaging system. The method comprising connecting an input of an energy storage system to a DC power source; connecting an output of an energy storage system to an X-ray generator of the imaging system; charging the energy storage system by supplying electrical energy from the DC power source; and outputting stored electrical energy from the energy storage system to the X-ray generator for powering the X-ray generator during an X-ray exposure.

DETAILED DESCRIPTION

Figure 1:
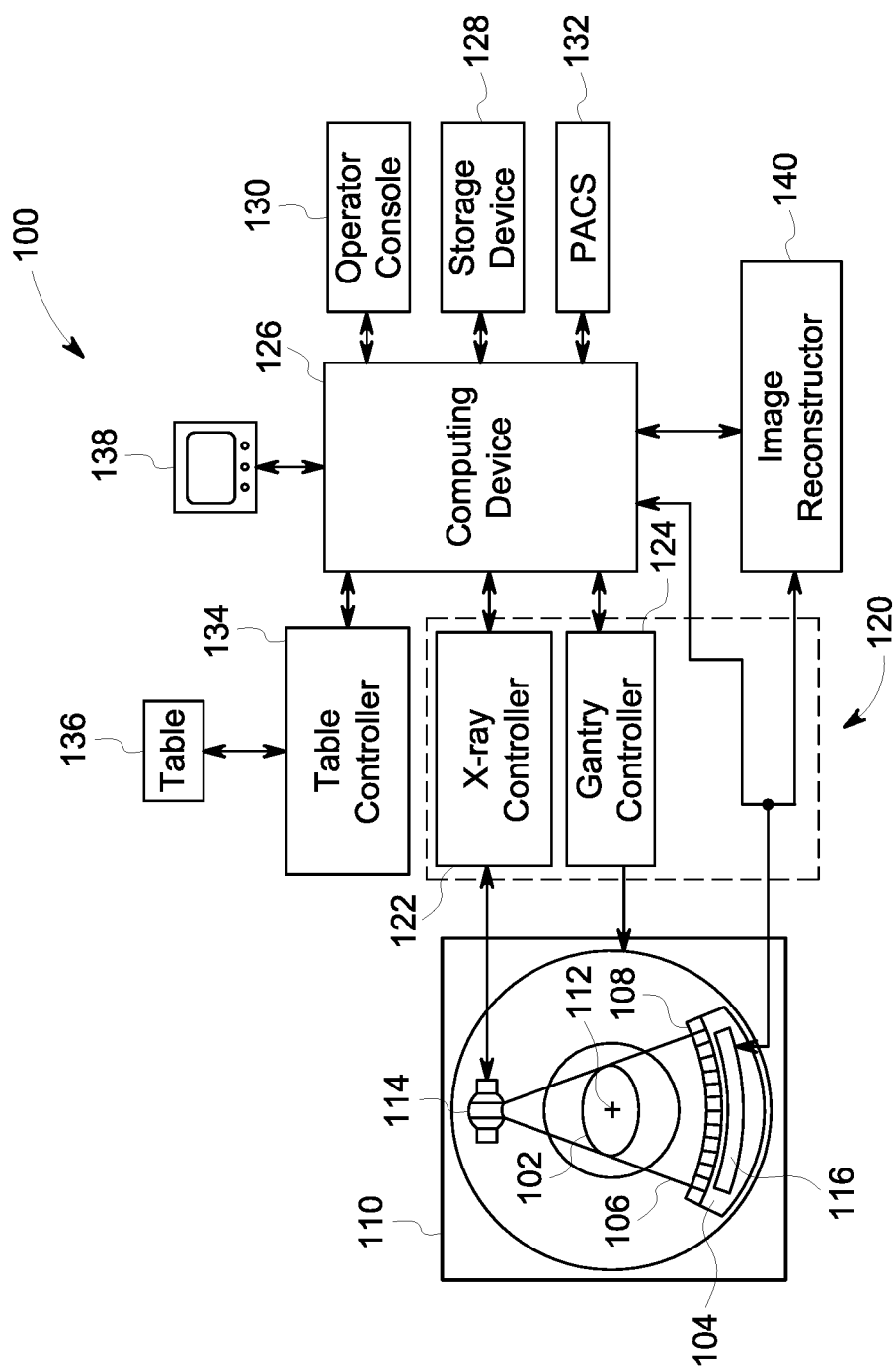
FIG. 1 shows a schematic block diagram of an exemplary imaging system according to an aspect of the disclosure.

In the following specification and the claims, reference will be made to a number of terms, which shall be defined to have the following meanings.

The singular forms "a", "an", and "the" include plural references unless the context clearly dictates otherwise.

As used herein, the terms "software" and "firmware" are interchangeable and include any computer program stored in memory for execution by devices that include, without limitation, mobile devices, tablets, clusters, computers, workstations, clients, and servers.

As used herein, the term "computer" and related terms, e.g., "computing device," "computer system," "processor," or "controller" are not limited to integrated circuits referred to in the art as a computer, but broadly refers to at least one central processing unit (CPU), graphics processing unit (GPU), microcontroller, microcomputer, programmable logic controller (PLC), application specific integrated circuit (ASIC), field-programmable gate array (FPGA) and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms "systems," "devices," and "apparatus" are interchangeable and include components, sub-components, sub-systems that include without limitation the X-ray imaging systems or computed tomography (CT) imaging systems.

It should be appreciated that, while the phrase energy storage system is broadly used herein to refer to a system comprising one or more batteries or supercapacitors for providing power for powering an imaging system for limited periods of time, the energy storage system described herein may comprise at least one battery or a plurality of batteries, configured as a battery pack or a plurality of supercapacitor modules, and therefore the phrases "energy storage system," "battery pack," and "supercapacitor modules" may be used interchangeably herein.

The following description relates to various embodiments of imaging systems. In particular, systems and methods are provided for powering a computed tomography (CT) imaging system. An example of a CT imaging system that may be used to acquire images in accordance with the present techniques is provided in FIG. 1. The CT imaging system may include at least one X-ray generator and at least one X-ray tube that consume a large amount of power when operated in certain imaging modes. The at least one X-ray generator supplies power to the at least one X-ray tube. In some instances, the power requirements of a CT imaging system including the at least one X-ray generator and at least one X-ray tube may exceed the power capacity of the electrical utility power supply of the building housing the CT imaging system and/or a power distribution unit (PDU) that transfers the alternating current (AC) of the electrical utility power to direct current (DC) for powering the CT imaging system. One approach to addressing the power requirements of the CT imaging system may include upgrading the electrical power utility, such as by increasing the size of cables, fuses, circuit breakers, and/or a distribution transformer. Another approach may include upgrading to a larger PDU or installing a second PDU. However, such solutions may be costly and time-consuming to the point of discouraging the use of a CT imaging system.

Figure 2:
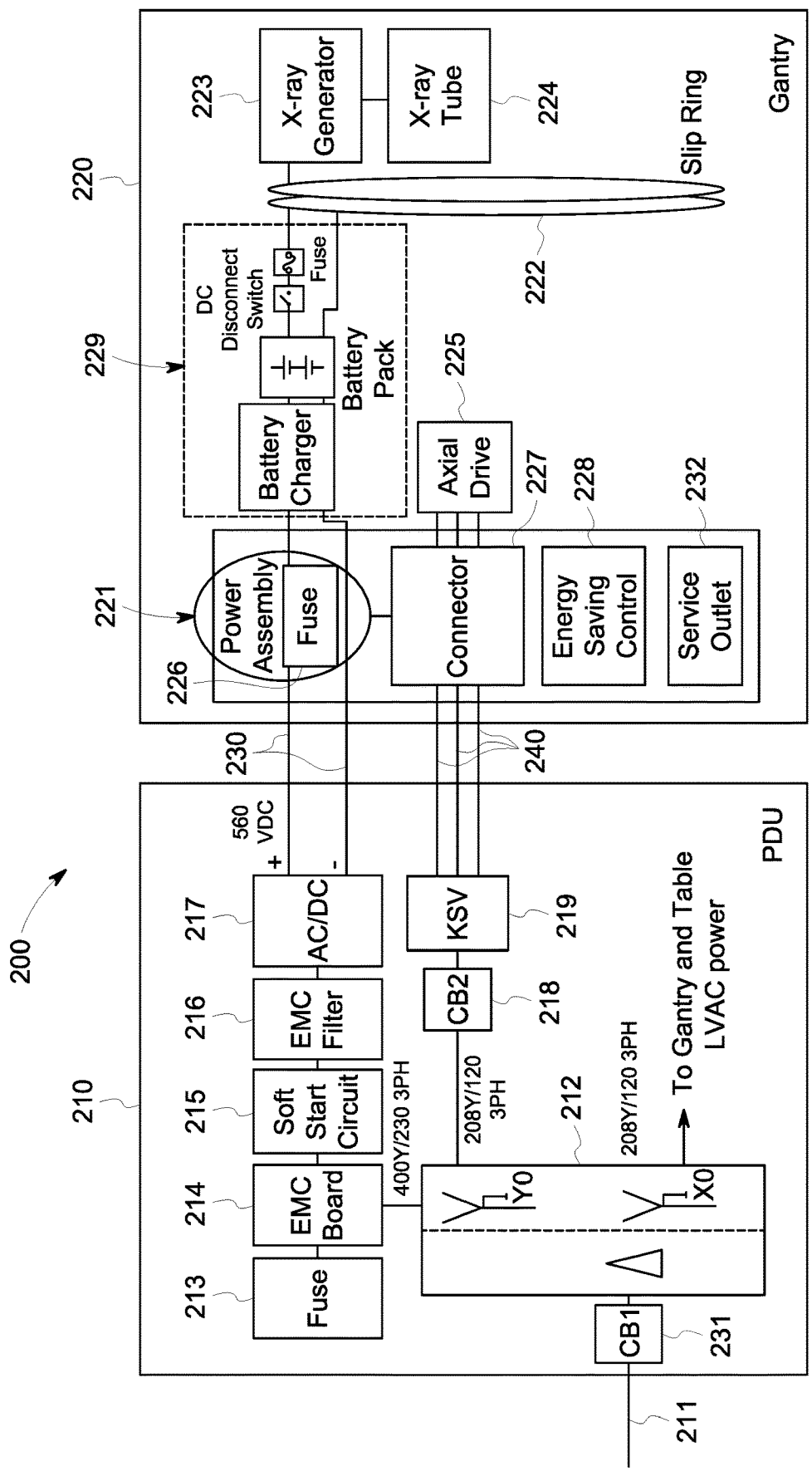
FIG. 2 shows a schematic block diagram of a power system including an energy storage system integrated within the gantry of a computed tomography (CT) imaging system according to an aspect of the disclosure.
Figure 3:
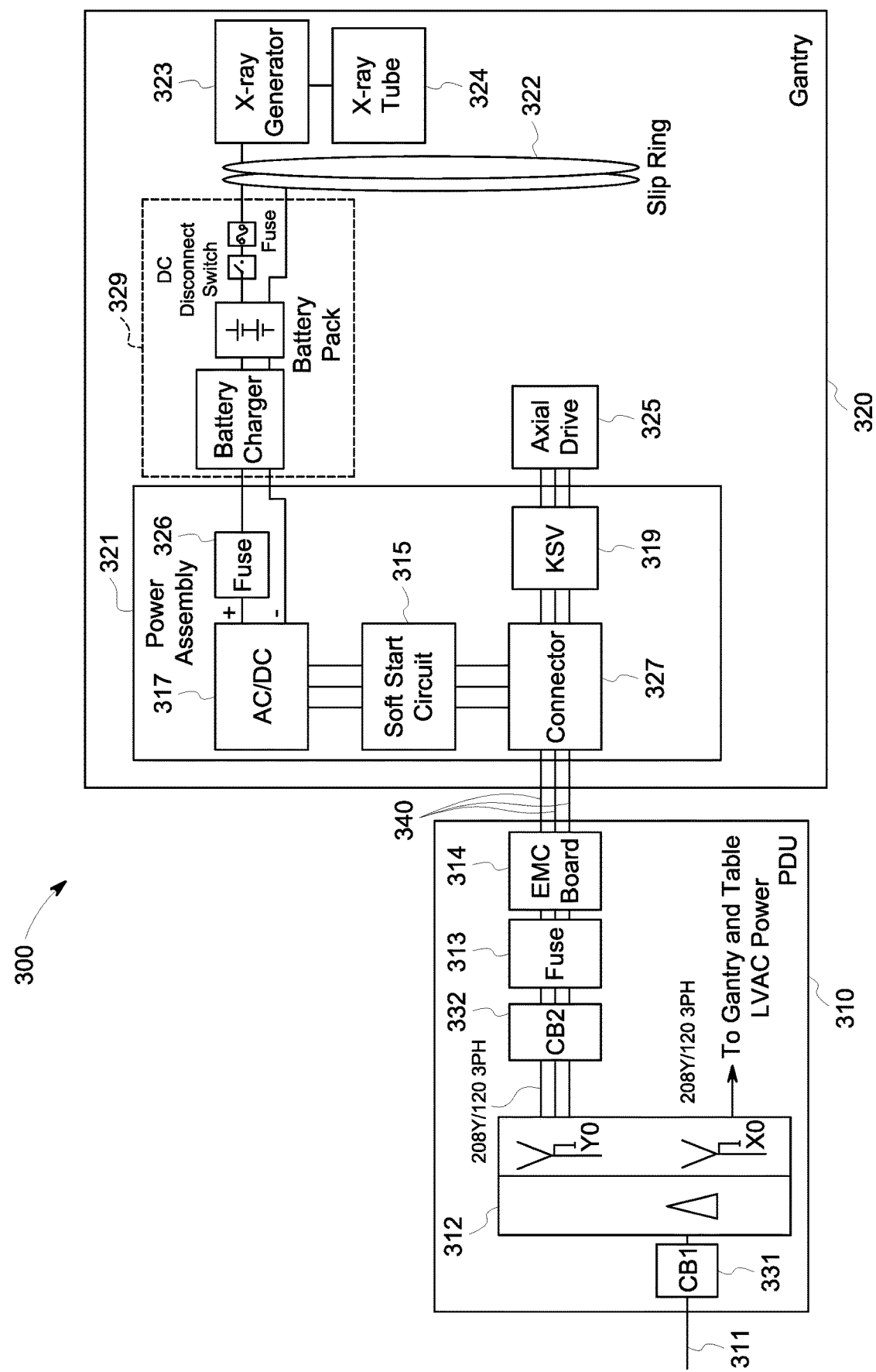
FIG. 3 shows a schematic block diagram of a power system including an energy storage system integrated within the gantry of a CT imaging system, with a three-phase AC power source coupled from a power distribution unit (PDU) to the gantry according to an aspect of the disclosure.
Figure 4:
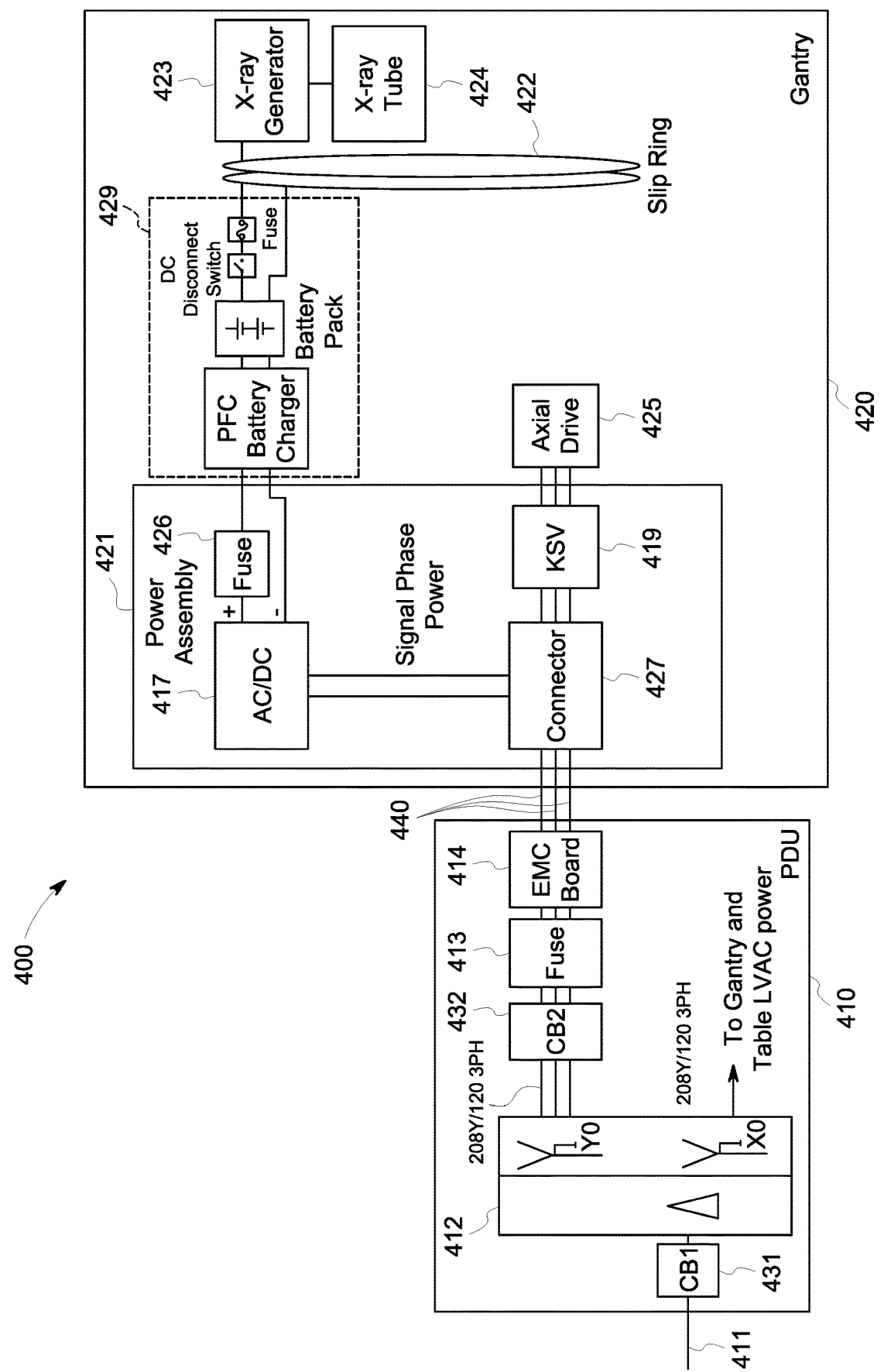
FIG. 4 shows a schematic block diagram of a power system including an energy storage system integrated within the gantry of a CT imaging system with a single-phase AC power source and a power factor correction (PFC) battery charger according to an aspect of the disclosure.
Figure 5:
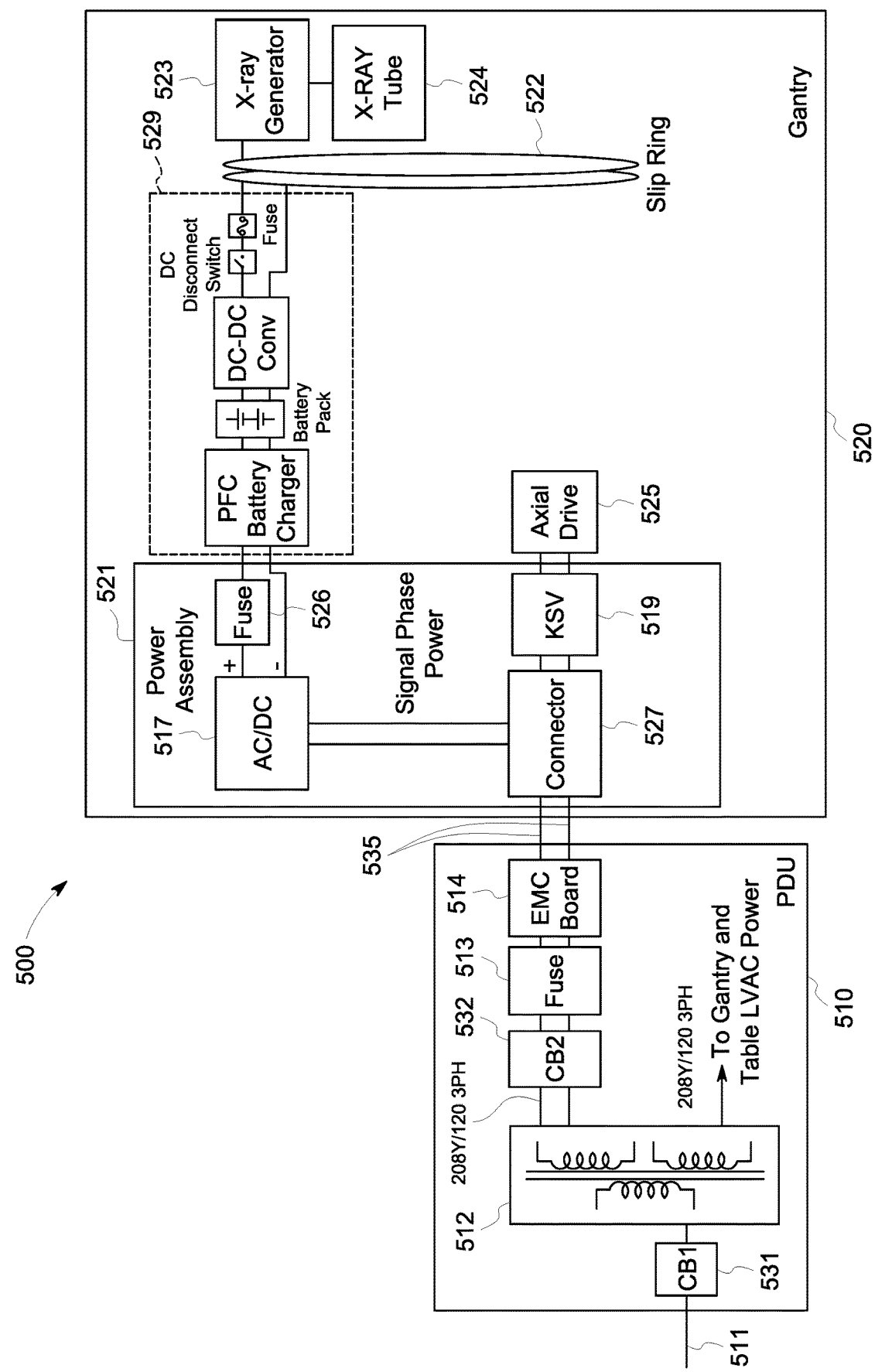
FIG. 5 shows a schematic block diagram of a power system including an energy storage system integrated within the gantry of a CT imaging system with a single-phase AC power source powering the PDU according to an aspect of the disclosure.

Another approach may include providing an energy storage system such as at least one battery or a plurality of batteries, configured as a battery pack or a plurality of supercapacitor modules, as shown in FIG. 2, to reduce peak load requirements of the electrical power utility. A battery pack may include one or more batteries as well as a control circuit for controlling the battery pack. Alternatively, a plurality of supercapacitors my include a control circuit for controlling the plurality of supercapacitors. It may also include a power circuit for powering components of the battery pack or supercapacitor modules, one or more fans for cooling components of the battery pack or supercapacitor modules, and a control switch for charging or discharging the battery pack or supercapacitor modules, as shown in FIGS. 3-5.

Figure 6:
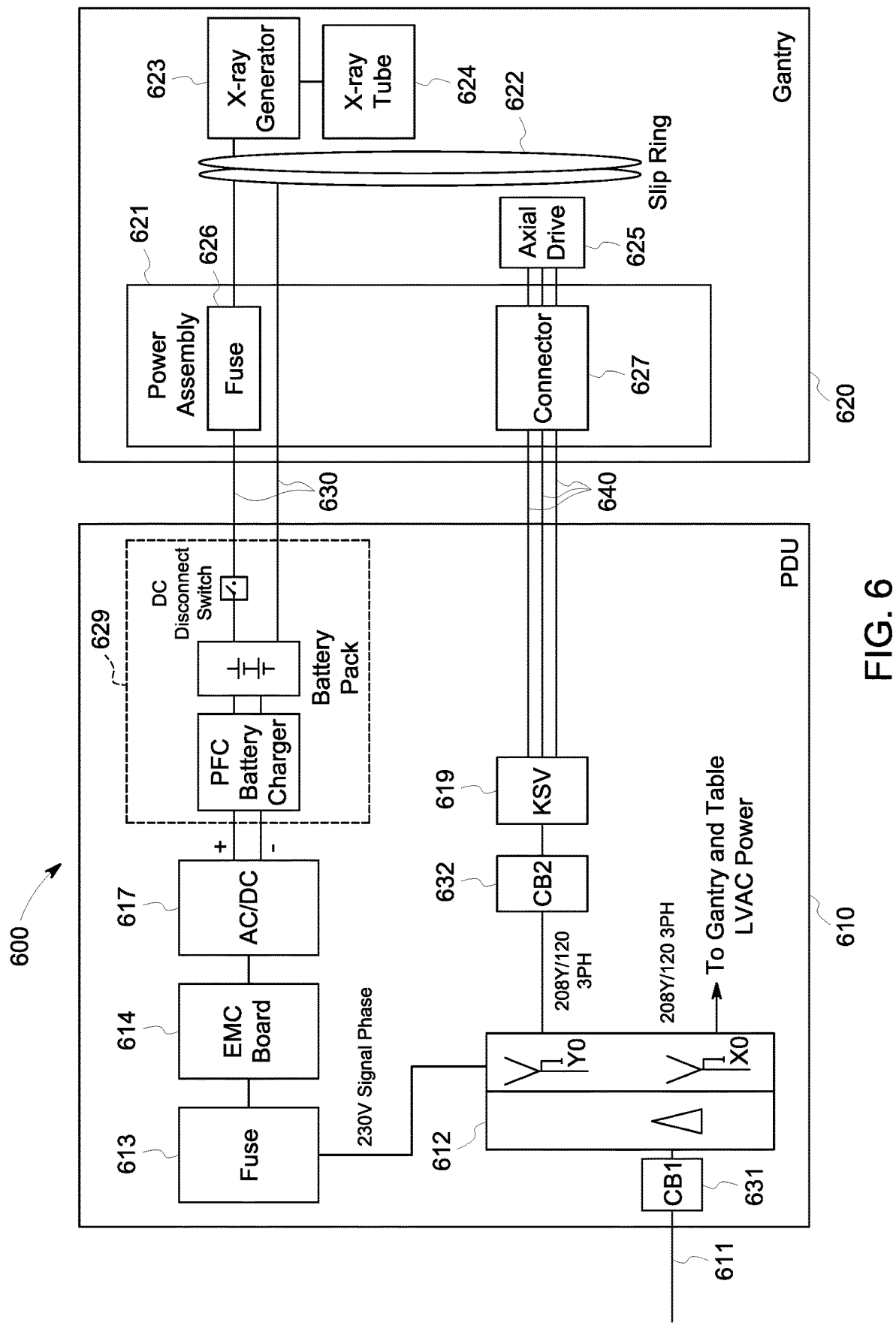
FIG. 6 shows a schematic block diagram of a power system including an energy storage system and a PFC battery charger integrated within the PDU according to an aspect of the disclosure.

The battery pack or supercapacitor modules as described herein may therefore provide power to one or more components of the CT imaging system during at least a portion of an X-ray exposure, as depicted in FIG. 6, to enable power consumption above the output limits of a PDU.

The energy storage system is electrically coupled to a DC bus and configured to store electrical energy output by the PDU. The energy storage system is configured to output the stored electrical energy to power the X-ray generator only during peak power requirements, such as an X-ray exposure. The energy storage system may include at least one battery or a plurality of batteries, which may be configured as a battery pack, that is included within a PDU of a CT imaging system. A control system may be included and employed to regulate the power supply during peak and the non-peak power consumption times. The energy storage system is configured to provide backup power for the CT imaging system, including the X-ray generator for powering the X-ray tube, the axial drive for rotating the CT imaging system gantry, and the other system electronics when there is a power failure or no available power. The battery pack may be incorporated within the PDU or the gantry of the CT imaging system. A battery charger may also be provided to charge the battery pack.

Although an X-ray or a CT imaging system is described by way of example, it should be understood that the present techniques may also be useful when applied to other imaging systems, such as a magnetic resonance (MR) imaging system, a positron emission tomography (PET) imaging systems, single-photon emission computed tomography (SPECT) imaging systems, an ultrasound imaging system, a fluoroscopic X-ray imaging system, and combinations thereof (e.g., multi-modality imaging systems, such as PET/CT, PET/MR or SPECT/CT imaging systems). The present discussion of a CT imaging system is provided merely as an example of one suitable imaging system.

Embodiments of the present disclosure will now be described, by way of example, with reference to the figures, in which FIG. 1 illustrates an exemplary imaging system 100, such as an X-ray imaging system or a CT imaging system. In accordance with aspects of the present disclosure, the imaging system 100 is configured for imaging a subject 102. In an exemplary embodiment, the imaging system 100 includes an X-ray detector array 104. The X-ray detector array 104 further includes a plurality of detector elements 108 that together sense an X-ray beam 106 that pass through the subject 102 such as a patient to acquire corresponding projection data. Accordingly, in an exemplary embodiment, the detector array 104 is fabricated in a multi-slice configuration including the plurality of rows of cells or detector elements 108. In such a configuration, one or more additional rows of the detector elements 108 are arranged in a parallel configuration for acquiring the projection data.

In certain embodiments, the imaging system 100 is configured to traverse different angular positions around the subject 102 for acquiring desired projection data. Accordingly, the gantry 110 and the components mounted thereon may be configured to rotate about a center of rotation 112 for acquiring the projection data, for example, at different energy levels. Alternatively, in embodiments where a projection angle relative to the subject 102 varies as a function of time, the mounted components may be configured to move along a general curve rather than along a segment of a circle.

As the X-ray source 114 and the X-ray detector array 104 rotate, the X-ray detector array 104 collects data of attenuated X-rays from the X-ray beam passing through the subject 102. The data collected by the X-ray detector array 104 undergoes processing to condition the data to represent the line integrals of the attenuation coefficients of the scanned subject 102. This data is commonly known as projection data.

In some examples, the individual detector elements 108 of the X-ray detector array 104 may comprise photon-counting detector elements which register the interactions of individual photons into one or more energy bins. It should be appreciated that the methods described herein may also be implemented with energy-integrating detectors.

The imaging system 100 may further include a controller system 120 to control components of the CT imaging system, such as rotation of the gantry 110 and the operation of the X-ray source 114. In certain embodiments, the controller system 120 may include an X-ray controller 122 configured to provide power and timing signals to the X-ray source 114. Additionally, the controller system 120 may include a gantry controller 124 configured to control the rotational speed and/or position of the gantry 110 based on imaging requirements.

The imaging system 100 further includes a data acquisition system (DAS) 116 configured to receive analog data from the detector elements 108 and convert the analog data to digital signals for subsequent processing. The data received and digitized by the DAS 116 is transmitted to a computer or computing device 126. In one example, the computing device 126 stores the data in a storage device 128. The storage device 128, for example, may include a hard disk drive, a floppy disk drive, a compact disk-read/write (CD-R/W) drive, a Digital Versatile Disc (DVD) drive, a flash drive, a solid-state storage drive, or other type of storage device.

Additionally, the computing device 126 provides commands and parameters to one or more of the DAS 116, the X-ray controller 122, and the gantry controller 124 for controlling system operations such as data acquisition and/or processing. In certain embodiments, the computing device 126 controls system operations based on operator input. The computing device 126 receives operator input, for example, including commands and/or scanning parameters via an operator console 130 operatively coupled to the computing device 126. The operator console 130 may include a keyboard (not shown), a touchscreen or other input device to allow the operator to specify commands and/or scanning parameters.

Although FIG. 1 illustrates only one operator console 130, more than one operator console may be coupled to the imaging system 100, for example, for inputting or outputting system parameters, initiating image acquisitions, and/or viewing images. Further, in certain embodiments, the imaging system 100 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In certain embodiments, for example, the imaging system 100 may either include or be coupled to a picture archiving and communications system (PACS) 132. In an exemplary implementation, the PACS 132 is further coupled to a remote system such as a radiology information system (RIS), hospital information system (HIS), and/or to an internal or external network (not shown) to allow operators at different locations to supply commands and parameters and/or gain access to the image data.

The computing device 126 uses the operator-supplied and/or system-defined commands and parameters to operate a table controller 134, which in turn, may control a table 136 which may be a motorized table. Particularly, the table controller 134 may move the table 136 for appropriately positioning the subject 102 in the gantry 110 for acquiring projection data corresponding to a region of interest (ROI) of the subject 102 being imaged.

As previously mentioned, the DAS 116 receives and digitizes projection data acquired by the detector elements 108. Subsequently, an image reconstructor 140 uses the sampled and digitized projection data to perform high-speed image reconstruction. Although FIG. 1 illustrates the image reconstructor 140 as a separate component, in certain embodiments, the image reconstructor 140 may form part of the computing device 126. Alternatively, the image reconstructor 140 may be absent from the imaging system 100 and instead the computing device 126 may perform one or more functions of the image reconstructor 140. Moreover, the image reconstructor 140 may be located locally or remotely and may be operatively connected to the imaging system 100 using a wired or wireless network. Particularly, one exemplary embodiment may use computing resources in a "cloud" network for the image reconstructor 140.

In an exemplary embodiment, the image reconstructor 140 may store the reconstructed images in the storage device 128. Alternatively, the image reconstructor 140 may transmit the reconstructed images to the computing device 126 for generating useful patient information for evaluation and diagnosis. In certain embodiments, the computing device 126 may transmit the reconstructed images and/or the patient information to a display 138 communicatively coupled to the computing device 126 and/or the image reconstructor 140.

The various methods and processes described further herein may be stored as executable instructions in non-transitory memory on a computing device in imaging system 100. In an exemplary embodiment, image reconstructor 140 may include such executable instructions in non-transitory memory and may apply the methods described herein to reconstruct an image from acquired scanning data. In another embodiment, computing device 126 may include the instructions in non-transitory memory, and may apply the methods described herein, at least in part, to a reconstructed image after receiving the reconstructed image from image reconstructor 140. In yet another embodiment, the methods and processes described herein may be distributed across image reconstructor 140 and computing device 126.

In an exemplary embodiment, the display 138 allows the operator to evaluate the imaged anatomy. The display 138 may also allow the operator to select a volume of interest (VOI) and/or request patient information, for example, via a graphical user interface (GUI) for a subsequent image acquisition scan or processing.

Generating X-rays from the X-ray source 114 requires a large amount of power. For example, the X-ray generator of a CT imaging system may require 24 kW of peak power (also called peak load) during X-ray generation or X-ray exposure while during times of no X-ray generation or no X-ray exposure, the X-ray generator consumes average power in the range of 200 W to 300 W. On an average day in a medical clinic, medical facility, hospital, or imaging facility, peak power consumption by the X-ray generator of a CT imaging system occurs only for a few minutes during a scan while the CT imaging systems may be operated for several hours a day. Accordingly, all of the other components of the power system that powers a CT imaging system needs to be designed with the peak power rating even though the peak power utilization only occurs for a relatively short period of time.

In addition, providing a backup power for the X-ray generator is also challenging considering the amount of peak power required by the CT imaging system and the space available to accommodate a battery pack within the CT imaging system.

FIG. 2 illustrates a schematic block diagram of a power system including an energy storage system integrated within the gantry of a CT imaging system according to an aspect of the disclosure. The energy storage system is configured to provide peak power to the X-ray generator and other components of the CT imaging system.

An exemplary power system 200 for powering a CT imaging system may include a power distribution unit (PDU) 210 electrically coupled to a CT imaging system gantry 220 for powering the X-ray generator 223 and other components of the CT imaging system. The PDU 210 having at least one input and at least two outputs, the at least one input electrically coupled to an alternating current (AC) power source 211 from a utility power supply. The PDU 210 may include all of the essential components for supplying regulated power, including but not limited to, an input AC power source 211, a first circuit breaker 231, a transformer 212, a first output from transformer 212 and a second output from the transformer 212. In an exemplary embodiment, the input AC power supply 211 from utility power source may be 200/220/240 volts alternating current (VAC) three-phase AC power, 380/400/420 VAC three-phase AC power, and/or 440/460/480 VAC three-phase AC power. The first output from transformer 212, providing 400/230 VAC three-phase AC power, may be coupled to a fuse 213, an electromagnetic compliance (EMC) board 214, a soft start circuit 215, an EMC filter 216, and an AC/DC circuit 217, providing 560 volts direct current (VDC) power to a direct current (DC) bus 230. The EMC board functions to reduce or eliminate EMC noise from the input AC power supply 211. The soft start circuit 215 functions to ensure a gradual power-on of the PDU 210 and to reduce capacitive inrush current when the PDU is turning on. In other words, a capacitor is used to reduce inrush current if a high voltage is applied across the capacitor, hence the soft start circuit ensures a slow build-up of voltage across the capacitor, which reduces inrush current. The EMC filter 216 also functions to reduce or eliminate EMC noise from the circuit. Therefore, the EMC filter 216 may not be necessary if the EMC board 214 is functioning to reduce or eliminate EMC noise from the circuit. The AC/DC circuit 217, which may include a three-phase bridge rectifier and electrolytic capacitor(s) at its output. A second output from transformer 212, providing 208/120 VAC three-phase AC power, and may be coupled to a second circuit breaker 218, and a KSV circuit 219, which may include a three-phase contactor to make or break the a three-phase AC bus 240 coupled to a connector 227 and an axial drive 225 responsible for CT imaging system gantry rotation. The AC bus 240 provides three-phase low voltage AC (LVAC) power for the axial drive 225. There may be another output from transformer 212 that provides three-phase LVAC power (208/120 three-phase VAC) to the CT imaging system gantry and table.

The PDU 210 is electrically coupled to the CT imaging system gantry 220 and other components of the CT imaging system. In an exemplary embodiment, the gantry 220 having at least two inputs, the at least two inputs electrically coupled to the at least two outputs of the PDU 210. In one aspect of the disclosure, a DC bus 230 and an AC bus 240 of the PDU 210 is electrically coupled to a power assembly 221, preferable located within the gantry 220, to supply DC and AC power from the PDU 210 to the gantry 220. The DC bus 230 may be coupled to a fuse 226 within power assembly 221 to provide DC power to a slip ring 222 and an X-ray generator 223. The DC bus provides high voltage DC (HVDC) power for X-ray generator 223. The X-ray generator 223 provides power and control signals to an X-ray tube 224. The fuse 226 may have a reduced fuse rating as the load is reduced for only battery charging by a battery charger in an energy storage system 229 as described below. The AC bus 240 may be electrically coupled to a connector 227 to provide three-phase AC power to an axial drive 225 for rotating the CT imaging system gantry. Further, the power assembly 221 may include other components, for example an energy saving control 228 and a service outlet 232.

In an exemplary embodiment, the fuse 226 includes an input for receiving DC power and an output for outputting DC power, and the connector 227 includes an input for receiving AC power and an output for outputting AC power.

The power system 200 may further include an energy storage system 229 that may be provided between the fuse 226 and the slip ring 222 to supply power to the slip ring 222 and the X-ray generator 223 during times when the AC power source 211 from the utility power supply is not available and during peak power requirements. The energy storage system 229 may include at least one input and at least one output. In an exemplary embodiment, the energy storage system 229 may include at least one battery or a plurality of batteries, configured as a battery pack or a plurality of supercapacitor modules. The at least one battery having an input and an output. In addition to the battery pack, the energy storage system 229 may include a battery charger having an input for receiving DC power and an output electrically coupled to the input of the at least one battery, a DC disconnect switch having an input electrically coupled to the output of the at least one battery, and a protection fuse. The fuse having an input electrically coupled to the output of the switch and an output electrically coupled to slip ring 222. In one example, a 560V DC output on the DC bus 230 from the PDU 210 may be electrically coupled to the energy storage system 229, particularly the battery charger for charging the battery pack within the energy storage system 229. The output from the energy storage system 229 may be connected to the slip ring 222 and the X-ray generator 223. The DC disconnector switch and the fuse provide control of the power coming from the battery pack and offer protection for the slip ring 222 and the X-ray generator 223. The battery pack within the energy storage system 229 may be utilized to power the X-ray generator 223 and the X-ray tube 224 only during X-ray generation or X-ray exposure, and during the time between two successive X-ray exposures, the battery pack may be charged by the battery charger. In case the battery pack fails or is drained of stored energy, the energy storage system may be bypassed, and power is supplied from the PDU directly to the CT imaging system gantry and X-ray generator.

Still referring to FIG. 2, in one aspect of the disclosure, the connector 227 may be connected to three-phase AC power from the PDU 210 through the AC bus 240 and the connector 227 may be configured to supply three-phase AC power to the axial drive 225 for rotating the CT imaging system gantry. The PDU 210 separates the AC power source 211 from utility power supply into DC power that is supplied on the DC bus 230 to power the X-ray generator 223, and into three-phase AC power that is supplied to the axial drive 225.

Introduction of the energy storage system 229 for powering the X-ray generator 223 eliminates the requirement of continuously providing peak power to the X-ray generator 223. The battery pack may provide the peak power required for X-ray generation only during an X-ray exposure. Further, the requirement of including the fuse 213, the EMC board 214, the soft start circuit 215, the EMC filter 216 at high peak power ratings may be eliminated, thereby reducing the cost of the PDU 210.

During operation, the battery pack may be discharged to a certain level during an X-ray exposure and may be charged back by the battery charger before the next X-ray exposure. In one example, the battery pack may be discharged to 7 to 10% of its energy storage capacity during one X-ray exposure and even if the battery pack is not fully charged to its 100% state of charge (SOC) level before the next X-ray exposure begins, the battery pack may still support more than ten or more X-ray exposures during back-to-back CT scans or X-ray exposures with a lesser amount of total power consumption.

Several varieties of batteries are commercially available that may be incorporated into the battery pack. Although there is no limitation on the configuration of the battery pack, a small size battery may have an energy storage capacity of about three to five times that of the energy required by the X-ray generator for a single scan. By cutting the peak load requirement, the electrical infrastructure required to support the X-ray generator may be reduced. There are many high energy density lithium-ion (Li-ion) batteries available in the market and many are evolving because of increasing demand for safe and high energy density batteries for other applications. A LiFePo4 type Li-ion battery is one of the safest technologies even though it has lesser energy density than other Li-ion technology (lithium cobalt oxide (LCO), lithium nickel cobalt aluminum oxide (NCA), etc.). A battery size calculation and a suitable size battery pack may be designed considering the battery performance parameters and requirements.

In one example, considering the average power requirement of 260 Watts (W) and the peak power requirement of 24 kW and in view of the scan protocols, the battery parameters may be defined. Considering the highest X-ray scan duration according to a protocol of 120 seconds and an X-ray generator efficiency of about 85%, a battery efficiency of about 90% and a maximum discharge current of about 60 Amps (A) may be required. In one example, the battery pack may be around 1800 WH (Watt Hour) with 560 VDC and size of the battery may be around 325×200×200 mm. A depleted battery charge due to power consumption by the X-ray generator may be recharged within ten minutes with a 1000 W battery charger. The energy storage system and the battery chargers may be made available with input power factor correction (PFC). The energy storage system may be incorporated in the gantry without modifying the PDU design.

According to another aspect of the disclosure, the PDU 210 may be simplified using the components with reduced power ratings. Reduced power rating of the components like the PDU transformer 212. The EMC board 213 may reduce the cost of the PDU and leverage the benefits of the energy storage system 229 on the gantry 220. The PDU 210 may be modified to reduce the cost of the electrical parts as the high voltage DC (HVDC) bus 230 need only provide the battery charging load (e.g., 1000 W). The PDU transformer 212, fuse 213, EMC board 214, soft start circuit 215, and other electrical components or circuits may be reduced in size according to the battery charging power requirement. This may reduce the PDU 210 cost. Similarly, the DC electrical components may be modified to single-phase parts as the power rating is in the range of 1 kW, and for larger CT imaging systems it may be around 3 kW.

FIG. 3 illustrates a schematic block diagram of a power system including an energy storage system integrated within the gantry of a CT imaging system, with a three-phase AC power supply coupled from a PDU to the gantry according to an aspect of the disclosure. In FIG. 3, the PDU and CT imaging system gantry electrical architecture are modified to reduce the cost of the power system for powering the CT imaging system.

An exemplary power system 300 for powering a CT imaging system may include a PDU 310 that may be simplified with only one three-phase AC output 340 to the gantry 320 instead of having two separate outputs, one output providing HVDC power for X-ray generator and another output providing LVAC power for the axial drive as shown in FIG. 2. Hence the three-phase AC bus 340 may be split at connector 327 into an axial drive three-phase LVAC power and an energy storage system HVDC power integrated within the gantry 320 as shown in FIG. 3. The cost of a separate HVDC power cable may be eliminated and control of the power system 300 simplified. However, the gantry 320 may need to accommodate few more electrical components, such as a soft start circuit 315, an AC/DC circuit 317, which may include a three-phase bridge rectifier and electrolytic capacitor(s), and a KSV circuit 319, which may include a bridge rectifier and electrolytic capacitor(s) that may be moved from the PDU 310 into the gantry 320.

The PDU 310 having at least one input and at least one output, the at least one input electrically coupled to an AC power source 311 from a utility power supply. The PDU 310 may include all of the essential components for supplying regulated power, including but not limited to, a first circuit breaker 331, a transformer 312, a first output from transformer 312 and a second output from the transformer 312. In an exemplary embodiment, the input AC power source 311 from utility power supply may be 200/220/240 VAC three-phase AC power, 380/400/420 VAC three-phase AC power, and/or 440/460/480 VAC three-phase AC power. The first output from transformer 312, providing LVAC 208/120 VAC three-phase AC power, may be coupled to a second circuit breaker 332, a fuse 313, and an EMC board 314, providing an output to AC bus 340. A second output from transformer 312, providing 208/120 VAC three-phase AC power may provide this three-phase LVAC power to the CT imaging system gantry and table.

The PDU 310 is electrically coupled to the CT imaging system gantry 320 and other components of the CT imaging system. In an exemplary embodiment, the gantry 320 having at least one input, the at least one input electrically coupled to the at least one output of the PDU 310. In one aspect of the disclosure, a three-phase AC bus 340 of the PDU 310 is electrically coupled to a power assembly 321, preferable located within the gantry 320 to supply AC power from the PDU 310 to the gantry 320. The three-phase AC bus 340 may be coupled to a connector 327 within power assembly 321. The connector 327 provides two outputs, a first three-phase AC output electrically coupled to a soft start circuit 315, an AC/DC circuit 317 and a fuse 326, providing 560 VDC power to an energy storage system 329. A second three-phase AC output is electrically coupled to a KSV circuit 319, which provides LVAC for powering an axial drive 325 for rotating the CT imaging system gantry. The three-phase AC bus 340 from the PDU 310 to the gantry 320 may be provided to reduce the number of cables needed from the PDU 310 to the gantry 320.

In an exemplary embodiment, the fuse 326 includes an input for receiving DC power and an output for outputting DC power, and the connector 327 includes an input for receiving AC power and an output for outputting AC power.

The output of fuse 326 is electrically coupled to the energy storage system 329. The fuse 326 may have a reduced fuse rating as the load is reduced for only battery charging by a battery charger in an energy storage system 329. The energy storage system 329 may include at least one input and at least one output. The energy storage system 329 may be provided between the fuse 326 and the slip ring 322 to supply HVDC power to the slip ring 322 and the X-ray generator 323 during times when the AC power source 311 from the utility power supply is not available and during peak power requirements. In an exemplary embodiment, the energy storage system 329 may include at least one battery or a plurality of batteries, configured as a battery pack or a plurality of supercapacitor modules. The at least one battery having an input and an output. In addition to the battery pack, the energy storage system 329 may include a battery charger having an input for receiving DC power and an output electrically coupled to the input of the at least one battery, a DC disconnect switch having an input electrically coupled to the output of the at least one battery, and a protection fuse. The fuse having an input electrically coupled to the output of the switch and an output electrically coupled to slip ring 322. The output from the energy storage system 329 may be electrically coupled to the slip ring 322 and the X-ray generator 323. The DC disconnector switch and the fuse provide control of the power coming from the battery pack and offer protection for the slip ring 322 and the X-ray generator 323. The battery pack within the energy storage system 329 may be utilized to power the X-ray generator 323 during an X-ray exposure, and during the time between two successive X-ray exposures, the battery pack may be charged by the battery charger. The battery pack may be discharged to a certain level during an X-ray exposure and may be charged back by the battery charger before the next X-ray exposure.

FIG. 4 illustrates a schematic block diagram of a power system including an energy storage system integrated within the gantry of a CT imaging system with a single-phase AC power source and a power factor correction (PFC) battery charger according to an aspect of the disclosure. The battery charger includes a PFC circuit and is configured as a PFC battery charger. The PFC battery charger is configured to charge the at least one battery or battery pack. In FIG. 4, the power assembly 421 is simplified with a single-phase AC power input to an AC/DC circuit 417, and a PFC battery charger for powering the X-ray generator of a CT imaging system. The PFC battery charger may reduce the power consumption and overall cost of the power system 400. The PFC battery charger reduces the reactive power consumption by the CT imaging system, improves the power factor, and results in lower electricity bills.

An exemplary power system 400 for powering a CT imaging system may include a PDU 410 that is electrically coupled to a CT imaging system gantry 420. The PDU 410 having at least one input and at least one output, the at least one input electrically coupled to an AC power source 411 from a utility power supply. The PDU 410 may include all of the essential components for supplying regulated power, including but not limited to, a first circuit breaker 431, a transformer 412, a first output from transformer 412 and a second output from the transformer 412. In an exemplary embodiment, the input AC power source 411 from utility power supply may be 200/220/240 VAC three-phase AC power, 380/400/420 VAC three-phase AC power, and/or 440/460/480 VAC three-phase AC power. The first output from transformer 412, providing LVAC 208/120 VAC three-phase AC power, may be coupled to a second circuit breaker 432, a fuse 413, and an EMC board 414, providing an output to AC bus 440. A second output from transformer 412, providing 208/120 VAC three-phase AC power may provide this three-phase LVAC power to the CT imaging system gantry and table.

The PDU 410 is electrically coupled to the CT imaging system gantry 420 and other components of the CT imaging system. In an exemplary embodiment, the gantry 420 having at least one input, the at least one input electrically coupled to the at least one output of the PDU 410. In one aspect of the disclosure, a three-phase AC bus 440 of the PDU 410 is electrically coupled to a power assembly 421, preferable located within the gantry 420 to supply AC power from the PDU 410 to the gantry 420. The three-phase AC bus 440 may be coupled to a connector 427 within power assembly 421. The connector 427 provides two outputs, a first single-phase AC output electrically coupled to an AC/DC circuit 417 and a fuse 426, providing 560 VDC power to an energy storage system 429. A second three-phase AC output is electrically coupled to a KSV circuit 419, which provides LVAC for powering an axial drive 425 for rotating the CT imaging system gantry.

In an exemplary embodiment, the fuse 426 includes an input for receiving DC power and an output for outputting DC power, and the connector 427 includes an input for receiving AC power and an output for outputting AC power.

The output of fuse 426 is electrically coupled to the energy storage system 429. The fuse 426 may have a reduced fuse rating as the load is reduced for only battery charging by a PFC battery charger in an energy storage system 429. The energy storage system 429 may include at least one input and at least one output. The energy storage system 429 may be provided between the fuse 426 and the slip ring 422 to supply HVDC power to the X-ray generator 423 during times when the AC power source 411 from the utility power supply is not available and during peak power requirements. In an exemplary embodiment, the energy storage system 429 may include at least one battery or a plurality of batteries, configured as a battery pack or a plurality of supercapacitor modules. The at least one battery having an input and an output. In addition to the battery pack, the energy storage system 429 may include a PFC battery charger having an input for receiving DC power and an output electrically coupled to the input of the at least one battery, a DC disconnect switch having an input electrically coupled to the output of the at least one battery, and a fuse. The fuse having an input electrically coupled to the output of the switch and an output electrically coupled to slip ring 422. The output from the energy storage system 429 may be electrically coupled to the slip ring 422 and the X-ray generator 423. The DC disconnector switch and the fuse provide control of the power coming from the battery pack and offer protection for the slip ring 422 and the X-ray generator 423. The battery pack within the energy storage system 429 may be utilized to power the X-ray generator 423 during an X-ray exposure, and during the time between two successive X-ray exposures, the battery pack may be charged by the PFC battery charger. The battery pack may be discharged to a certain level during an X-ray exposure and may be charged back by the PFC battery charger before the next X-ray exposure.

In existing CT imaging systems, the PDU may experience a peak load of approximately 40 kVA and it is not commercially viable to incorporate PFC circuitry in the PDU. Therefore, in an exemplary embodiment, the energy storage system 429 powers the X-ray generator 423 and eliminates the requirement of supplying peak power and the PDU 410 may operate only at an average load.

FIG. 5 illustrates a schematic block diagram of a power system including an energy storage system integrated within the gantry of a CT imaging system with a single-phase AC power source powering the PDU according to an aspect of the disclosure.

An exemplary power system 500 for powering a CT imaging system may include a PDU 510 that is electrically coupled to a CT imaging system gantry 520. The PDU 510 having at least one input and at least one output, the at least one input electrically coupled to an AC power source 511 from a utility power supply. The PDU 510 may include all of the essential components for supplying regulated power, including but not limited to, an input AC power source 511 from utility power supply, a first circuit breaker 531, a transformer 512, a first output from transformer 512 and a second output from the transformer 512. In an exemplary embodiment, the input AC power source 511 from utility power supply may be 110/220 VAC single-phase AC power. The first output from transformer 512, providing LVAC 208/120 VAC three-phase AC power, may be coupled to a second circuit breaker 532, a fuse 513, and an EMC board 514, providing an output to AC bus 530. A second output from transformer 512, providing 208/120 VAC three-phase AC power may provide this three-phase LVAC power to the CT imaging system gantry and table.

The PDU 510 is electrically coupled to the CT imaging system gantry 520 and other components of the CT imaging system. In an exemplary embodiment, the gantry 520 having at least one input, the at least one input electrically coupled to the at least one output of the PDU 510. In one aspect of the disclosure, a three-phase AC bus 535 of the PDU 410 is electrically coupled to a power assembly 521, preferable located within the gantry 520 to supply AC power from the PDU 510 to the gantry 520. The three-phase AC bus 535 may be coupled to a connector 527 within power assembly 521. The connector 527 provides two outputs, a first single-phase AC output electrically coupled to an AC/DC circuit 517 and a fuse 526, providing 560 VDC power to an energy storage system 529. A second three-phase AC output is electrically coupled to a KSV circuit 519, which provides LVAC for powering an axial drive 525 for rotating the CT imaging system gantry.

In an exemplary embodiment, the fuse 526 includes an input for receiving DC power and an output for outputting DC power, and the connector 527 includes an input for receiving AC power and an output for outputting AC power.

The output of fuse 526 is electrically coupled to the energy storage system 529. The fuse 526 may have a reduced fuse rating as the load is reduced for only battery charging by a PFC battery charger in an energy storage system 529. The energy storage system 529 may include at least one input and at least one output. The battery charger includes a PFC circuit and is configured as a PFC battery charger. The PFC battery charger is configured to charge the at least one battery or battery pack. The energy storage system 529 may be provided between the fuse 526 and the slip ring 522 to supply HVDC power to the X-ray generator 523 during times when the AC power source 511 from the utility power supply is not available and during peak power requirements. In an exemplary embodiment, the energy storage system 529 may include at least one battery or a plurality of batteries, configured as a battery pack or a plurality of supercapacitor modules. The at least one battery having an input and an output. In addition to the battery pack, the energy storage system 529 may include a PFC battery charger having an input for receiving DC power and an output electrically coupled to the input of the at least one battery, DC_DC converter, a DC disconnect switch having an input electrically coupled to the output of the at least one battery, and a fuse. The fuse having an input electrically coupled to the output of the switch and an output electrically coupled to slip ring 522. The output from the energy storage system 529 may be electrically coupled to the slip ring 522 and the X-ray generator 523. The DC disconnector switch and the fuse provide control of the power coming from the battery pack and offer protection for the slip ring 522 and the X-ray generator 523. The battery pack within the energy storage system 529 may be utilized to power the X-ray generator 523 during an X-ray exposure, and during the time between two successive X-ray exposures, the battery pack may be charged by the PFC battery charger. The battery pack may be discharged to a certain level during an X-ray exposure and may be charged back by the PFC battery charger before the next X-ray exposure.

At the connector 527, the three-phase line may be split into two separate power lines one each to power the axial drive 525 and the battery charger. The AC power from the PDU 510 may be converted to DC using an AC/DC circuit 517. Accordingly, the cost of the high voltage direct current (HVDC) cable to the gantry 520 may be saved and control may be simplified.

The single-phase AC power supply 511 may scale down the input supply requirement of the PDU 510 from 40 kVA to 4 kVA and components within the PDU 510 may have lower power ratings. Further, instead of connecting the battery pack directly to the DC disconnect switch, a boost type DC-DC converter may be incorporated between the battery pack and the DC disconnect switch. This DC-DC converter may boost a 48 VDC battery supply to a 560 VDC X-ray generator input voltage, and the requirement of high voltage battery pack may be avoided.

FIG. 6 illustrates a schematic block diagram of a power system including an energy storage system integrated within the PDU of a CT imaging system according to an aspect of the disclosure. The energy storage system is configured to provide peak power to the X-ray generator and other components of the CT imaging system. In FIG. 6, to keep the gantry design unchanged, the energy storage system may be located within the PDU. In this embodiment, the PDU is highly simplified with a reduced size transformer, a fuse, an EMC board, and an AC/DC circuit. Even after adding the energy storage system into the PDU, the PDU's overall cost will be reduced at least by 20% from the current PDU cost because of the reduction in power rating of the electrical components.

An exemplary power system 600 for powering a CT imaging system may include a PDU 610 electrically coupled to a CT imaging system gantry 620 for powering the X-ray generator 623 and other components of the CT imaging system. The PDU 610 having at least one input and at least two outputs, the at least one input electrically coupled to an AC power source 611 from a utility power supply. The PDU 610 may include all of the essential components for supplying regulated power, including but not limited to, an input alternating current (AC) power source 611 from utility power supply, a first circuit breaker 631, a transformer 612, a first output from transformer 612 and a second output from the transformer 612. In an exemplary embodiment, the input AC power source 611 from utility power supply may be 200/220/240 VAC three-phase AC power, 380/400/420 VAC three-phase AC power, and/or 440/460/480 VAC three-phase AC power. The first output from transformer 612, providing 230 VAC single-phase AC power, may be coupled to a fuse 613, an EMC board 614, and an AC/DC circuit 617, providing 560 VDC power to an energy storage system 629 located within the PDU 610. A second output from transformer 612, providing 208/120 VAC three-phase AC power, and may be coupled to a second circuit breaker 632, and a KSV circuit 619, which may include a three-phase contactor to make or break the a three-phase AC bus 640 coupled to a connector 627 and an axial drive 625 responsible for CT imaging system gantry rotation. The AC bus 640 provides three-phase low voltage AC (LVAC) power for the axial drive 625. There may be another output from transformer 612 that provides three-phase LVAC power (208/120 three-phase VAC) to the CT imaging system gantry and table.

The power system 600 may further include an energy storage system 629 included within the PDU 610 and provided at the output of the AC/DC 617, providing 560 VDC power to an energy storage system 629. The energy storage system 629 may include at least one input and at least one output. In an exemplary embodiment, the energy storage system 629 may include at least one battery or a plurality of batteries, configured as a battery pack or a plurality of supercapacitor modules. The at least one battery having an input and an output. In addition to the battery pack, the energy storage system 629 may include a PFC battery charger having an input for receiving DC power and an output electrically coupled to the input of the at least one battery, and a DC disconnect switch having an input electrically coupled to the output of the at least one battery and an output electrically coupled to a fuse 626 in the power assembly 621 in the gantry 620. The fuse 626 having an input electrically coupled to the output of the switch and an output electrically coupled to slip ring 622. In one example, a 560V DC output on the DC bus 630 from the PDU 610 may be electrically coupled to the power assembly 621, particularly a fuse 626 for powering an X-ray generator 623. The battery pack within the energy storage system 229 may be utilized to power the X-ray generator 623 and the X-ray tube 624 only during X-ray generation or X-ray exposure, and during the time between two successive X-ray exposures, the battery pack may be charged by the battery charger. In case the battery pack fails or is drained of stored energy, the energy storage system may be bypassed, and power is supplied from the PDU directly to the CT imaging system gantry and X-ray generator.

The PDU 610 is electrically coupled to the CT imaging system gantry 620 and other components of the CT imaging system. In an exemplary embodiment, the gantry 620 having at least two inputs, the at least two inputs electrically coupled to the at least two outputs of the PDU 610. In one aspect of the disclosure, a DC bus 630 and an AC bus 640 of the PDU 610 is electrically coupled to a power assembly 621, preferable located within the gantry 620, to supply DC and AC power from the PDU 610 to the gantry 620. The DC bus 630 may be coupled to a fuse 626 within power assembly 621 to provide DC power to a slip ring 622 and an X-ray generator 623. The DC bus provides high voltage DC (HVDC) power for X-ray generator 623. The X-ray generator 623 provides power and control signals to an X-ray tube 624. The AC bus 640 may be electrically coupled to a connector 627 to provide three-phase AC power to an axial drive 625 for rotating the CT imaging system gantry.

In an exemplary embodiment, the fuse 626 includes an input for receiving DC power and an output for outputting DC power, and the connector 627 includes an input for receiving AC power and an output for outputting AC power.

Several varieties of batteries are commercially available that may be incorporated into the battery pack. Although there is no limitation on the configuration of the battery pack, a small size battery may have an energy storage capacity of about three to five times that of the energy required by the X-ray generator for a single scan. By cutting the peak load requirement, the electrical infrastructure required to support the X-ray generator may be reduced. There are many high energy density lithium-ion (Li-ion) batteries available in the market and many are evolving because of increasing demand for safe and high energy density batteries for other applications. A LiFePo4 type Li-ion battery is one of the safest technologies even though it has lesser energy density than other Li-ion technology (lithium cobalt oxide (LCO), lithium nickel cobalt aluminum oxide (NCA), etc.). A battery size calculation and a suitable size battery pack may be designed considering the battery performance parameters and requirements.

Operation of the CT imaging system includes a method for providing peak power for the CT imaging system. The method includes coupling an energy storage system to an X-ray generator of the CT imaging system. The energy storage system may include a plurality of batteries, configured as a battery pack that may include a battery charger for charging the plurality of batteries, a DC disconnect switch and a fuse. The method further comprises charging the energy storage system by electrical energy supplied from a direct current (DC) bus. The battery pack may be charged using the battery charger that may comprise a power factor correction (PFC) circuit. This may reduce the reactive power consumption by the CT system, hence lowering electricity bills. In one example, a 560 VDC output on a DC bus may be utilized for charging the battery using the battery charger and the battery pack may be connected to an X-ray generator with fuse protection and DC disconnector switch for controlling energy storage power supply. In one example, if a 1000 W battery charger is used, it will draw the current of 2.22 A (considering a lower DC bus voltage of 450 VDC) from the PDU via a 560 VDC bus. The battery pack may be discharged to a certain level during the X-ray exposure and may be charged back by the battery charger before the next X-ray exposure. In one example, each X-ray exposure may consume about 7-10% of the total storage energy of the battery and even if the battery is not charged to its 100% complete state of charge (SOC) level before the next scan begins, still it may support more than ten back-to-back scans.

The method further comprises outputting electrical energy for powering the X-ray generator through the DC bus only during an X-ray exposure. In an X-ray imaging system, such as a CT imaging system, the X-ray generator consumes high peak power for a short time, but the average power consumed is less. In one example, a 24 kW X-ray generator consumes around 200-300 W average power for 25 scans per day and all of the upstream components must be of higher power ratings to supply this peak power (24 kW). In another example, a CT imaging system having an average power rating of 6.3 KVA, but a peak power rating of 40 KVA. Hence the 33 KVA extra power requirement is for the X-ray generator to power the X-ray tube for short time periods during X-ray generation.

According to an aspect of the disclosure, the battery pack may provide the peak power required for powering the X-ray tube only during X-ray generation. The requirement of supplying peak power for powering the X-ray tube during an X-ray exposure may be eliminated with the addition of an energy storage system. A plurality of batteries may be incorporated into a battery pack for supplying power to the X-ray generator, which supplies power to the X-ray tube during X-ray generation. Other electrical components of the CT imaging system may be powered from the AC bus from the PDU. Accordingly, the batteries and battery pack size may be optimized to only provide peak power for X-ray generation, thereby minimizing battery cost, space requirements, and dependency on the utility power supply. The battery pack may shave the peak load (e.g., 33 KVA) which is required for the X-ray generator. The batteries and battery pack of a suitable size and high discharge current capability may be placed either in the CT imaging system gantry or in the PDU to provide peak power for X-ray generation and the rest of the CT imaging system may be powered by conventional AC power. The electrical components may be modified to single-phase components as the power rating may be just nearly 1 kW and for larger CT imaging systems that require more power it may be around 2-3 kW. The batteries of the battery pack may be charged with a suitable battery charger during non-X-ray generation time. Further, the method may comprise directly powering the X-ray generator by bypassing the energy storage system similar to the conventional method in the situation where the battery pack fails or is completely discharged, as power may be supplied to the X-ray generator directly from the PDU.

The method may further comprise providing a three-phase AC power output to the gantry and splitting the AC power into powering an axial drive and an energy storage system. The PDU design may be simplified with only one three-phase AC power output instead of having two separate AC power outputs, one for creating HVDC power for the X-ray generator and one for creating LVAC power for the axial drive. This may reduce the cost of the power system and power control may be simplified. However, the gantry may need to accommodate a few more electrical components, which would be moved from the PDU into the gantry.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A power system for powering an imaging system, comprising:
    a power distribution unit (PDU) having at least one input and at least one output, the at least one input electrically coupled to an alternating current (AC) power source from a utility power supply;
    a gantry of the imaging system having at least one input, the at least one input electrically coupled to the at least one output of the PDU; and
    an energy storage system providing peak power to an X-ray generator of the imaging system during X-ray generation; wherein the energy storage system comprises:
    at least one battery having an input and an output;
    a battery charger having an input for receiving DC power and an output electrically coupled to the input of the at least one battery, the battery charger configured to charge the at least one battery;
    a switch having an input electrically coupled to the output of the at least one battery and an output operable to supply stored electrical energy from the at least one battery to the X-ray generator.

2. The power system of claim 1, wherein the energy storage system includes at least one input and at least one output, and wherein the at least one input receives direct current (DC) power and the at least one output provides DC power to the X-ray generator.

3. The power system of claim 1, wherein the imaging system is a computed tomography (CT) imaging system.

4. The power system of claim 1, wherein the energy storage system is located within the gantry.

5. The power system of claim 1, wherein the energy storage system is located within the PDU.

6. The power system of claim 1, further comprising a power assembly located within the gantry, the power assembly including a fuse and a connector, wherein the fuse includes an input for receiving DC power and an output for outputting DC power, and wherein the connector includes an input for receiving AC power and an output for outputting AC power.

7. The power system of claim 6, wherein the at least one output of the PDU is a three-phase AC bus electrically coupled to and supplying AC power to the power assembly.

8. The power system of claim 6, wherein the at least one output of the PDU is a DC bus electrically coupled to and supplying DC power to the power assembly.

9. The power system to claim 1, wherein the battery charger includes a power factor correction (PFC) circuit and is configured as a PFC battery charger, and wherein the PFC battery charger is configured to charge the at least one battery.

10. The power system to claim 1, wherein the at least one battery is a lithium-ion battery.

11. An imaging system, comprising:
a PDU with an input electrically coupled to a three-phase AC power source and at least one output;
an imaging system gantry with at least one input electrically coupled to the at least one output of the PDU; and
an energy storage system configured to store electrical energy and output the stored electrical energy to power an X-ray generator during an X-ray exposure; wherein the energy storage system comprises:
at least one battery having an input and an output;
a battery charger having an input for receiving DC power and an output electrically coupled to the input of the at least one battery, the battery charger configured to charge the at least one battery;
a switch having an input electrically coupled to the output of the at least one battery and an output operable to supply stored electrical energy from the at least one battery to the X-ray generator.

12. The imaging system of claim 11, wherein the imaging system gantry includes a power assembly.

13. The imaging system of claim 11, wherein the energy storage system is located within the imaging system gantry.

14. The power system of claim 11, wherein the energy storage system is located within the PDU.

15. The imaging system of claim 11, wherein the imaging system is a CT imaging system.

* * * * *